US006541756B2

(12) United States Patent
Schulz et al.

(10) Patent No.: US 6,541,756 B2
(45) Date of Patent: Apr. 1, 2003

(54) SHIELDED OPTICAL PROBE HAVING AN ELECTRICAL CONNECTOR

(75) Inventors: Christian E. Schulz, Rancho Santa Margarita, CA (US); Ammar Al-Ali, Tustin, CA (US); Eugene E. Mason, La Mirada, CA (US); Mike A. Mills, Golden, CO (US)

(73) Assignee: Masimo Corporation, Irvine, CA (US)

( * ) Notice: Subject to any disclaimer, the term of this patent is extended or adjusted under 35 U.S.C. 154(b) by 126 days.

(21) Appl. No.: 09/770,757

(22) Filed: Jan. 25, 2001

(65) Prior Publication Data

US 2001/0045532 A1 Nov. 29, 2001

Related U.S. Application Data

(63) Continuation-in-part of application No. 09/708,251, filed on Nov. 7, 2000, now Pat. No. 6,280,213, which is a continuation of application No. 09/318,563, filed on May 26, 1999, now abandoned, which is a continuation of application No. 08/838,392, filed on Apr. 9, 1997, now Pat. No. 5,934,925, which is a continuation of application No. 08/543,297, filed on Oct. 16, 1995, now Pat. No. 5,645,440, application No. 09/770,757, which is a continuation-in-part of application No. 09/420,544, filed on Oct. 19, 1999, and a continuation-in-part of application No. 09/404,060, filed on Sep. 23, 1999, now Pat. No. 6,349,228, which is a continuation-in-part of application No. 09/021,957, filed on Feb. 11, 1998, now Pat. No. 5,995,855, application No. 09/770,757, which is a continuation-in-part of application No. 09/094,202, filed on Jun. 9, 1998, now Pat. No. 6,256,523, which is a continuation-in-part of application No. 08/543,789, filed on Oct. 16, 1995, now Pat. No. 5,782,757, which is a continuation-in-part of application No. 08/333,132, filed on Nov. 1, 1994, now Pat. No. 5,638,818, which is a continuation-in-part of application No. 07/672,890, filed on Mar. 21, 1991, now abandoned.

(51) Int. Cl.[7] ............................................. H01J 40/14
(52) U.S. Cl. ....................... 250/221; 250/239; 356/41
(58) Field of Search .............................. 250/559.4, 221, 250/227.24, 227.25, 239, 214 R; 356/40, 41; 600/323, 322, 310–318; 128/633–634; 385/76, 8, 92

(56) References Cited

U.S. PATENT DOCUMENTS

| 2,567,926 A | 9/1951 | Dunkelberger |
| 3,103,214 A | 9/1963 | Smith |
| 3,313,290 A | 4/1967 | Chance et al. |
| 3,319,216 A | 5/1967 | McClullough |

(List continued on next page.)

FOREIGN PATENT DOCUMENTS

| AU | 85938/91 | 4/1992 |
| AU | 664175 | 10/1992 |

(List continued on next page.)

OTHER PUBLICATIONS

US 4,928,691, 5/1990, Nicolson et al. (withdrawn).
http://www.masimo.com/system.htm, "System Overview & Performance", 2 pages, reviewed on Sep. 17, 1999.

(List continued on next page.)

*Primary Examiner*—Que T. Le
(74) *Attorney, Agent, or Firm*—Knobbe, Martens, Olson & Bear LLP

(57) ABSTRACT

The invention is a noninvasive optical probe having an electrical connector for connecting the optical probe to a cable connector. According to one embodiment, the electrical connector includes a durable flexible tab suspended between the housing of the optical probe and a protective cover. The electrical connector also advantageously forms, according to various embodiments, a flexible, plugable, lockable, removable, and sealable electrical connection.

43 Claims, 7 Drawing Sheets

U.S. PATENT DOCUMENTS

| | | |
|---|---|---|
| 3,463,142 A | 8/1969 | Harte |
| 3,482,565 A | 12/1969 | Gowen |
| 3,534,310 A | 10/1970 | Pelissier |
| 3,704,706 A | 12/1972 | Herczfeld et al. |
| 3,710,303 A | 1/1973 | Gallagher, Jr. |
| 3,711,272 A | 1/1973 | Randall et al. |
| 3,970,353 A | 7/1976 | Kaufman |
| 3,995,209 A | 11/1976 | Weston |
| 4,129,124 A | 12/1978 | Thalmann |
| 4,305,401 A | 12/1981 | Reissmueller et al. |
| 4,321,930 A | 3/1982 | Jobsis et al. |
| 4,334,544 A | 6/1982 | Hill et al. |
| 4,350,165 A | 9/1982 | Striese |
| 4,380,240 A | 4/1983 | Jöbsis et al. |
| 4,406,289 A | 9/1983 | Wesseling et al. |
| 4,414,980 A | 11/1983 | Godfrey |
| 4,451,694 A | 5/1984 | Harper et al. |
| 4,490,003 A | 12/1984 | Robinson |
| 4,498,722 A | 2/1985 | Fedder et al. |
| 4,505,848 A | 3/1985 | Kobayashi |
| 4,528,986 A | 7/1985 | Arundel et al. |
| 4,531,795 A | 7/1985 | Sinclair |
| 4,621,643 A | 11/1986 | New, Jr. et al. |
| 4,636,786 A | 1/1987 | Haertling |
| 4,642,627 A | 2/1987 | Hodsdon |
| 4,684,245 A | 8/1987 | Goldring |
| 4,685,464 A | 8/1987 | Goldberger et al. |
| 4,690,492 A | 9/1987 | Beard |
| 4,695,258 A | 9/1987 | Hanson et al. |
| 4,700,708 A | 10/1987 | New, Jr. et al. |
| 4,770,179 A * | 9/1988 | New et al. |
| 4,797,125 A | 1/1989 | Malana |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,838,808 A | 6/1989 | Fujiura |
| 4,844,784 A | 7/1989 | Suzuki et al. |
| 4,859,057 A | 8/1989 | Taylor et al. |
| 4,865,038 A | 9/1989 | Rich et al. |
| 4,867,165 A | 9/1989 | Noller et al. |
| 4,880,304 A | 11/1989 | Jaeb et al. |
| 4,907,594 A | 3/1990 | Muz |
| 4,913,150 A | 4/1990 | Cheung et al. |
| 4,927,264 A | 5/1990 | Shiga et al. |
| 4,938,218 A | 7/1990 | Goodman et al. |
| 4,952,177 A | 8/1990 | Drake et al. |
| 4,961,711 A | 10/1990 | Fujiura et al. |
| 4,964,408 A | 10/1990 | Hink et al. |
| 4,974,591 A | 12/1990 | Awazu et al. |
| 5,007,704 A | 4/1991 | McCartney |
| RE33,643 E | 7/1991 | Isaacson et al. |
| 5,031,608 A | 7/1991 | Weinsten |
| 5,058,588 A | 10/1991 | Kaestle |
| 5,080,098 A | 1/1992 | Willett et al. |
| 5,086,229 A | 2/1992 | Rosenthal et al. |
| 5,087,242 A | 2/1992 | Petelenz et al. |
| 5,090,410 A | 2/1992 | Saper et al. |
| 5,099,842 A | 3/1992 | Mannheimer et al. |
| 5,108,298 A | 4/1992 | Simmel |
| 5,109,848 A | 5/1992 | Thomas et al. |
| 5,109,849 A | 5/1992 | Goodman et al. |
| 5,125,403 A | 6/1992 | Culp |
| 5,170,786 A | 12/1992 | Thomas et al. |
| 5,209,230 A | 5/1993 | Swedlow et al. |
| 5,217,013 A | 6/1993 | Lewis et al. |
| 5,224,478 A | 7/1993 | Sakai et al. |
| 5,224,882 A | 7/1993 | Olms |
| 5,246,003 A | 9/1993 | DeLonzor |
| 5,247,931 A | 9/1993 | Norwood |
| 5,249,576 A | 10/1993 | Goldberger et al. |
| 5,287,853 A | 2/1994 | Vester et al. |
| 5,295,852 A | 3/1994 | Renn et al. |
| 5,295,872 A | 3/1994 | Christensson |
| 5,302,133 A | 4/1994 | Tondreault |
| 5,309,908 A | 5/1994 | Friedman et al. |
| 5,313,940 A | 5/1994 | Fuse et al. |
| 5,337,744 A | 8/1994 | Branigan |
| 5,380,213 A | 1/1995 | Piorunneck et al. |
| 5,387,122 A | 2/1995 | Goldberger et al. |
| 5,390,670 A | 2/1995 | Centa et al. |
| 5,407,368 A | 4/1995 | Strand et al. |
| 5,415,629 A | 5/1995 | Henley |
| 5,438,986 A | 8/1995 | Disch et al. |
| 5,452,717 A | 9/1995 | Branigan et al. |
| 5,469,845 A | 11/1995 | DeLonzor et al. |
| 5,498,235 A | 3/1996 | Flower |
| 5,509,823 A | 4/1996 | Harting et al. |
| 5,520,177 A | 5/1996 | Ogawa et al. |
| 5,521,997 A | 5/1996 | Rovenolt et al. |
| 5,569,823 A | 10/1996 | Schreier et al. |
| 5,584,296 A | 12/1996 | Cui et al. |
| 5,588,427 A | 12/1996 | Tien |
| 5,638,818 A | 6/1997 | Diab et al. |
| 5,645,440 A | 7/1997 | Tobler et al. |
| 5,660,567 A | 8/1997 | Nierlich et al. |
| 5,758,644 A | 6/1998 | Diab et al. |
| 5,782,757 A | 7/1998 | Diab et al. |
| 5,807,247 A | 9/1998 | Mechant et al. |
| 5,807,248 A | 9/1998 | Mills |
| 5,810,724 A | 9/1998 | Gronvall |
| 5,817,010 A | 10/1998 | Hibl |
| 5,818,985 A | 10/1998 | Merchant et al. |
| 5,895,369 A | 4/1999 | Flower |
| 5,919,133 A | 7/1999 | Taylor et al. |
| 5,934,925 A | 8/1999 | Tobler et al. |
| 5,939,609 A | 8/1999 | Knapp et al. |
| 5,970,353 A | 10/1999 | Sultan |
| 5,995,855 A | 11/1999 | KIani et al. |
| 6,256,523 B1 | 7/2001 | Diab et al. |

FOREIGN PATENT DOCUMENTS

| | | |
|---|---|---|
| CA | 2052650 | 4/1992 |
| DE | 3711272 | 10/1987 |
| DE | 36 19 442 A1 | 12/1987 |
| EP | 0 074 428 A1 | 3/1983 |
| EP | 0 262 779 A1 | 4/1988 |
| EP | 329196 | 8/1989 |
| EP | 0 404 562 A3 | 12/1990 |
| EP | 91 308738 | 9/1991 |
| EP | 0 481 612 A1 | 4/1992 |
| EP | 92116140 | 9/1992 |
| EP | 0 538 631 A1 | 4/1993 |
| EP | 0 745 348 | 12/1996 |
| EP | 0 832 598 A | 4/1998 |
| EP | 0 576 560 B1 | 5/2000 |
| EP | 0 790 800 B1 | 8/2000 |
| JP | 52031736 | 10/1977 |
| JP | 02017462 | 1/1990 |
| JP | 10314149 | 12/1998 |
| JP | 11053662 | 2/1999 |
| JP | 11185193 | 9/1999 |
| RU | 2096985 | 11/1997 |
| WO | 92 01894 | 7/1990 |
| WO | 62 01894 | 6/1992 |
| WO | 92 16142 | 10/1992 |
| WO | PCT/US95/14785 | 3/1996 |
| WO | WO 97/23159 | 7/1997 |
| WO | PCT/US00/22849 | 12/2000 |
| WO | WO 01/13790 A1 | 3/2001 |
| WO | PCT/US01/04265 | 6/2001 |

OTHER PUBLICATIONS http://www.masimo.com/pandt.htm, "Products & Technology", 1 page, reviewed on Sept. 17, 1999.

http://www.masimo.com/cables.htm, "Patient Cables", 1 page, reviewed on Sep. 17, 1999.

http://www.mashim.com/adt.htm, "Inop–adt—Adult Disposable Digit Sensor", 1 page, reviewed on Sep. 17, 1999.

http://www.mrequipment.com/products/pulse—oximetry.htm, "MR Equipment Magnetic Resonance Equipment Corporation, Pulse Oximetry in MRI Model 3500 Pulse Oximeter", 2 pages, Reviewed on Sep. 17, 1999.

http://www.mrequipment.com/products/oximetry_patient_mntrg.htm, "MR Equipment Magnetic Resonance Equipment Corporation, MR–Compatible High–Performance Optical Fiber Sensors, Pulse Oximetry Sensors for MRI Optic Sensors for use with MR–Compatible Pulse Oximeter", 2 pages, reviewed on Sep. 17, 1999.

Article entitled "Masimo Corporation, Discrete Staturation Transform Example", reviewed on Sep. 17, 1999.

http://www.dalsemi.com/, "Dallas Semiconductor", p. 1 only, reviewed on Jan. 12, 2000.

http://www.dalsemi.con/Prod—info/AudolD/index.html, "Dallas Semiconductor Automatic Information Overview", 10 pages, reviewed on Jan. 12, 2000.

Awtrey, "Sensor: The Journal of Applied Sensing Technology, Transmitting Data and Power over a One–Wire Bus", 4 pages, Feb. 1997.

Dallas Semiconductor, Application Note 30, "Recording Power Cycling Information Using the DS 1602/DS 1603", pages 7–9, 1993. Month Unkown.

Dallas Semiconductor, "DS 1602 Elapsed Time Counter", pp. 468–476, 1993.

Dallas Semiconductor, "DS 1603 Elapsed Time Counter Module", pp. 477–484, 1993. Month Unknown.

Dallas Semiconductor, "DS2401 Silicon Serial Number", 10 pages, Oct. 21, 1999.

Dallas Semiconductor, "DS2502 1Kbit Add–Only Memory", pp. 149–169, 1993. Month Unknown.

* cited by examiner

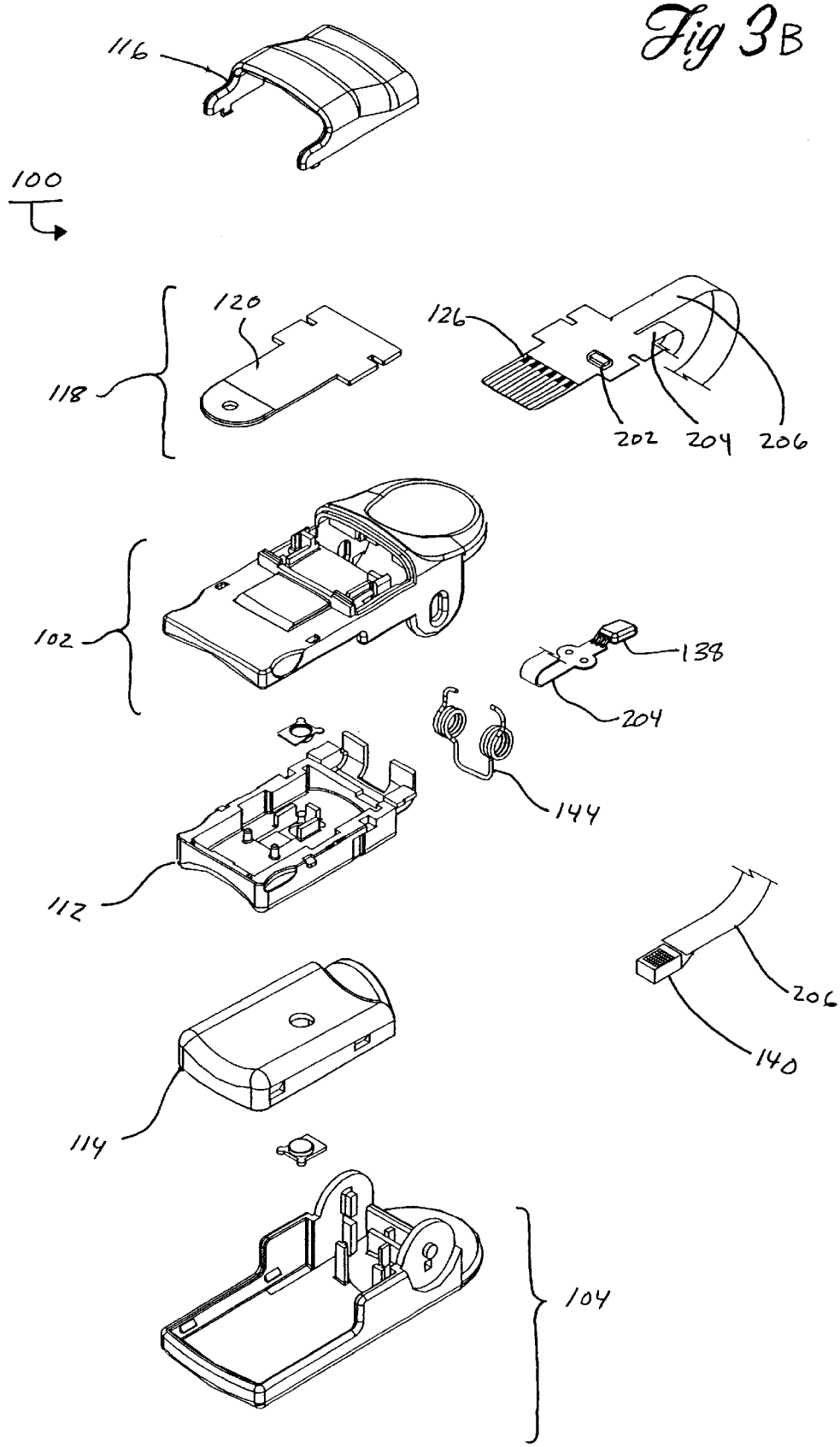

SHIELDED OPTICAL PROBE HAVING AN ELECTRICAL CONNECTOR

REFERENCE TO RELATED APPLICATIONS

The present application claims priority benefit under 35 U.S.C. §122 to the following pending patent applications in the following manner, all of which are incorporated herein by reference. The present application is a continuation-in-part of U.S. patent application Ser. No. 09/420,544, filed Oct. 19, 1999, entitled "SHIELDED OPTICAL PROBE AND METHOD". The present application is also continuation-in-part of U.S. patent application Ser. No. 09/094,202, filed Jun. 9, 1998, now U.S. Pat. No. 6,256,523 entitled "LOW-NOISE OPTICAL PROBES," which is a continuation of U.S. patent application Ser. No. 08/543,789, filed Oct. 16, 1995, entitled "LOW-NOISE OPTICAL PROBES," now U.S. Pat. No. 5,782,757, which is a continuation-in-part of U.S. patent application Ser. No. 08/333,132, filed Nov. 1, 1994, entitled "LOW NOISE OPTICAL PROBE," now U.S. Pat. No. 5,638,818, which is a continuation-in-part of U.S. patent application Ser. No. 07/672,890, filed Mar. 21, 1991, entitled "LOW NOISE OPTICAL PROBE," now abandoned. Further, the present application is a continuation-in-part of U.S. patent application Ser. No. 09/404,060, filed Sep. 23, 1999, now U.S. Pat. No. 6,349,228 entitled "PULE OXIMETRY SENSOR ADAPTER," which is a continuation of U.S. patent application Ser. No. 09/021,957, filed Feb. 11, 1998, entitled "PULSE OXIMETRY SENSOR ADAPTER," now U.S. Pat. No. 5,995,855. In addition, the present application is also continuation-in-part of U.S. patent application Ser. No. 09/708,251, U.S. Pat. No. 6,280,213, filed Nov. 7, 2000, entitled "PATIENT CABLE CONNECTOR," which is a continuation of U.S. patent application Ser. No. 09/318,563, filed May 26, 1999 now abandoned, entitled "PATIENT CABLE CONNECTOR," which is a continuation of U.S. patent application Ser. No. 08/838,392, filed Apr. 9, 1997, entitled "PATIENT CABLE CONNECTOR," now U.S. Pat. No. 5,934,925 which is a continuation of U.S. patent application Ser. No. 08/543,297, filed Oct. 16, 1995, entitled "PATIENT CABLE CONNECTOR," now U.S. Pat. No. 5,645,440.

BACKGROUND OF THE INVENTION

1. Field of the Invention

The present invention relates in general to low-noise optical probes which use optical energy to determine the characteristics of a medium, and in particular to optical probes having flexible, secure connectors for communicating signals to and from the probe.

2. Description of the Related Art

Electromagnetic, light or acoustic signals with known characteristics, when transmitted through or reflected in a medium, may reveal important information about that medium. In the field of medical testing and diagnosis, for example, light, heat or sound signals may be directed at a patient, transmitted or reflected through the patient's body, and received and compared with the original signal or wave. As a result, information about the patient's condition can be deduced without invasive testing, and information can be gathered continuously with minimal patient discomfort. For example, during surgery, blood oxygen saturation can non-invasively be deduced and continuously monitored.

Typically, reusable and disposable optical probes are employed to measure an amount of transmitted or reflected light through an accessible part of the body, such as a finger, an earlobe, loose skin, a forehead, or the like. For example, reusable and disposable optical probes or sensors having the foregoing characteristics are disclosed and described in U.S. Pat. No. 5,782,757.

The foregoing sensors typically incorporate a light source such as a lightemitting diode (LED) placed on one side of the body part, and a photodetector placed on an opposite side of the body part. The sensor may also connect to external monitoring equipment through a wire or cable. For example, reusable sensors often connect to external monitoring equipment through a permanent, plastic molded connection between the sensor and the cable.

The foregoing sensors suffer from at least several drawbacks. For example, the sensor is often limited to the useful life of the permanent plastic molded wire in that when the wire fails, the sensor is rendered inoperable despite its continuing functionality. Likewise, when the sensor fails, the wire or cable, the cost of which may not be trivial, is also rendered useless. In addition, existing reusable sensors do not have the capability to connect to monitoring equipment in a secure, reusable, yet flexible manner.

SUMMARY OF THE INVENTION

Based on at least the foregoing, there is a present need for an optical probe or having an electrical connector designed to connect the sensor to external monitoring equipment in a secure, reusable, yet flexible manner. According to one embodiment, the optical probe is usable with a patient cable connector designed to engage disposable or reusable/disposable (resposable) optical probes.

In one aspect of the invention, an improved optical probe assembly is disclosed which incorporates an electrical connector. The electrical connector includes a flexible plastic tab, on which is placed a flexible circuit. The plastic tab and circuit are typically at least partially enclosed in a protective housing. A separate patient cable connector attaches to the electrical connector via the flexible plastic tab, and a wire or other communications link connects the patient cable connector to external monitoring equipment. According to one embodiment, the electrical connector mates the patient cable connector in a manner that prevents incorrect engagement that may damage portions of the optical probe or patient cable connector.

In another aspect of the invention, an improved optical probe is disclosed having an electrical connector. According to one embodiment, once the patient cable connector has been connected to the electrical connector, the flexible plastic tab is locked into place within the patient cable connector via a locking aperture on the flexible plastic tab. The resulting connection is flexible, but electrically secure.

In another aspect of the invention, an improved optical probe assembly is disclosed with an electrical connector designed to accept connections to various external monitoring equipment and may accept connections using various types of wires. Thus, the patient cable connector may be connected to, for example, a wireless transmitter and/or battery, eliminating the need for a wire at all. Additionally, the type of wire may be varied based on patient needs, and the replacement of wires and patient cable connector may take place separately as needed from the replacement of optical probes.

In another aspect of the invention, an improved optical probe assembly is disclosed having an electrical connector adaptable for use with patient cable connectors designed for disposable, reusable, durable, and combination reusable/disposable sensors. Through the use of a standardized or universal patient cable connectors, optical sensors are advantageously used interchangeably and easily adapted to different monitoring equipment and patient conditions.

In another aspect of the invention, an improved optical probe assembly is disclosed with an electrical connector which is protected from fluids and the environment surrounding the sensor. Additionally, both a patient cable connector and protective housing over the electrical connector include shielding to prevent leakage of electromagnetic radiation which otherwise might interfere with operation of the optical probe.

In yet another aspect of the invention, an improved optical probe is disclosed with an electrical connector. The optical probe includes an improved pivoting mechanism around the finger such that the internal geometry of the light source, finger material, and photodetector are subject to less variation from finger movement. In addition, the optical probe provides more consistent pressure on the finger throughout the mechanism, uses fewer parts, includes a more straightforward assembly, and is less expensive to achieve appropriate geometry and pressure results.

Therefore, an aspect of the invention is an optical probe for irradiating tissue and producing a signal indicative of a physiological parameter of the tissue. The optical probe comprises a housing substantially securing a light source and a detector to tissue at a measurement site, thereby allowing the detector to produce a signal indicative of at least one physiological parameter of the tissue. The optical probe also comprises a plugable electrical connector forming a releasable connection with a cable connector, wherein the electrical connector includes a plurality of conductive paths electrically communicating with the light source and the detector. The cable connector electrically communicates with external monitoring equipment.

Another aspect of the invention is a reusable pulse oximetry sensor for producing a signal indicative of at least one physiological parameter of tissue. The sensor comprises an upper housing having a first circuit element comprising one of a light source and detector, and a first wire connected to the first circuit element. The sensor also comprises a lower housing having a second circuit element comprising the other of the light source and the detector, and a second wire connected the second circuit element. The sensor also comprises a hinge-like joint adjustably coupling the upper housing and lower housing and an electrical connector having a tab and a flexible circuit mounted on the tab and comprising a plurality of conductive paths. One of the conductive paths electrically connects to the first wire while another of the conductive paths electrically connects to the second wire, thereby providing an electrical connection from the conductive paths of the electrical connector to the light source and the detector.

Another aspect of the invention is a reusable pulse oximetry sensor for producing a signal indicative of at least one physiological parameter of tissue. The sensor comprises an upper housing having a first circuit element comprising one of a light source and a detector, and a lower housing having a second circuit element comprising the other of the light source and the detector. The sensor also comprises a hinge-like joint adjustably coupling the upper housing and lower housing, and an electrical connector having a tab, and a flexible circuit mounted on the tab and comprising a plurality of conductive paths. One of the conductive paths electrically connects to the detector while another of the conductive paths electrically connects to the light source.

Another aspect of the invention is an optical probe for non-invasively collecting a signal indicative of a physiological parameter of tissue. The optical probe comprises a light source, a detector, a connector having a flexible circuit mounted on a durable tab, and a protective housing at least partially covering the flexible circuit mounted on the durable tab.

Another aspect of the invention is a method of determining a physiological parameter of tissue using a non-invasive optical probe. The method comprises positioning a light source of a non-invasive optical probe to irradiate a measurement site with light, and positioning a detector of the probe to detect light which interacts with the measurement site. The method also comprises releasably connecting an external monitoring equipment cable to the probe through a flexible circuit mounted on a durable tab having a protective cover. Also, at least one the conductive paths electrically communicates with the light source and at least one of the conductive paths electrically communicates with the detector.

Another aspect of the invention is an electrical connector, comprising a flexible durable tab configured to guide a cable connector around the tab, thereby engaging the electrical connector to the cable connector. The connector also comprises a flexible circuit mounted on the flexible tab and electrically communicating with electrical contacts of the cable connector. The connector also comprises a locking mechanism releasably locking the electrical connector to the cable connector, and a protective cover covering at least a portion of the flexible circuit.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

FIG. 3B is an exploded view of the optical probe of FIG. 1, according to aspects of another embodiment of the present invention.

DETAILED DESCRIPTION OF THE PREFERRED EMBODIMENT

The invention is described in detail below with references to the figures, where like elements are referenced with like numerals throughout. The term probe and sensor are used interchangeably herein.

Figure 1:
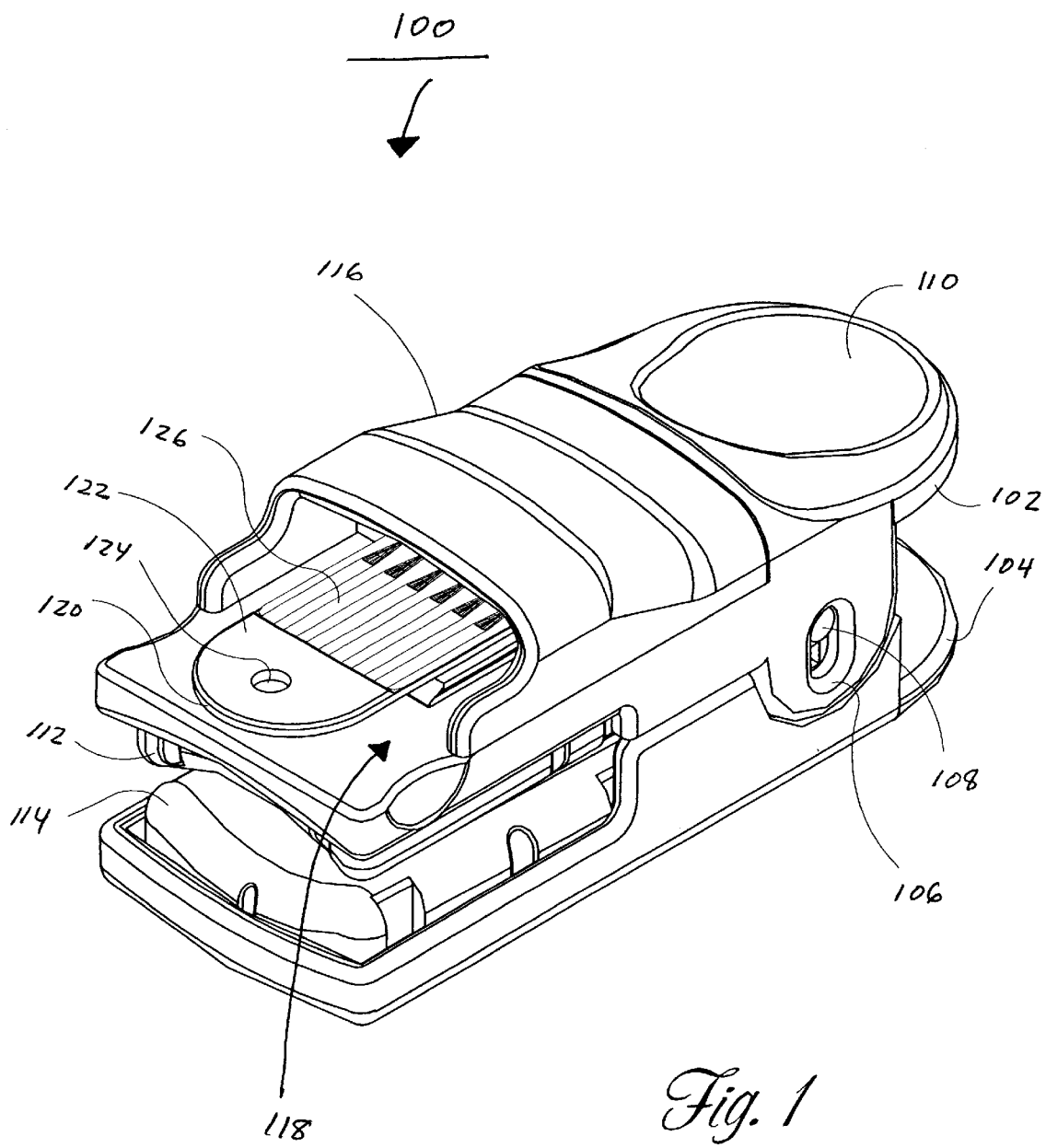
FIG. 1 is a perspective view of an optical probe with an electrical connector according to aspects of one embodiment of the present invention.

FIG. 1 illustrates an optical probe 100 according to an embodiment of the invention. As shown in FIG. 1, the optical probe 100 comprises an upper housing 102 and a lower housing 104. According to this embodiment, the upper housing 102 and the lower housing 104 oppose one another and are configured to include components designed to accept a measurement site for the tissue of a patient. For example, according to the embodiment shown in FIG. 1, the optical probe 100 is configured to accept a digit of a patient as a measurement site.

According to one embodiment, the upper and lower housings, 102 and 104, comprise injection moldable thermoplastic material or other suitable medium. As further illustrated in FIG. 1, the upper housing 102 comprises a aperture 106 while the lower housing 104 further comprises a pivoting element 108. According to one embodiment, the aperture 106 and the pivoting element 108 combine to form a hinge-like joint where the hinge-like joint allows the upper housing 102 to pivot from the lower housing 104 through a central axis defined, for example, by the pivoting element 108. Thus, according this embodiment, an open end of optical probe 100 opens as the upper housing 102 pivots away from the lower housing 104, thereby providing an area designed to accept tissue to be measured. According to one embodiment, the upper housing 102 and the lower housing 104 may each advantageously include a finger recess surface 110 formed to provide a comfortable, securing edge where, for example, medical staff or the user may advantageously squeeze a pivoting end of the optical probe 100, thereby opening the open end thereof.

Although the foregoing is described with reference to preferred and alternative embodiments, a skilled artisan will recognize from the disclosure herein that the optical probe 100 may comprise a wide number of mechanical devices designed to substantially secure the upper housing 102 and the lower housing 104 to a measurement site in a manner sufficient for the optical probe 100 to perform reliable measurements. Such mechanical devices may replace or work in conjunction with the foregoing hinge-like joint.

According to yet another embodiment of the invention, the upper housing 102 further comprises an upper support surface 112, while the lower housing 104 further comprises a lower support surface 114. According to this embodiment, the upper support surface 112 and the lower support surface 114 provide additional supporting structure for tissue when the tissue is placed in the optical probe 100. For example, as shown in FIG. 1, the upper and lower support surfaces, 112 and 114, are configured to accept a digit in a manner that is comfortable for the patient, advantageously helps substantially secure the optical probe 100 to a measurement site on the digit, provides at least a partial seal against ambient light, and provides for relatively straightforward replacement, sterilization, or both.

According to one embodiment, the upper and lower support surfaces, 112 and 114, comprise injection moldable thermoplastic elastomer material or other suitable medium. FIG. 1 also illustrates the optical probe 100 having a protective housing 116 and an electrical connector 118, according to aspects of yet another embodiment of the invention. As shown in FIG. 1, the protective housing 116 comprises a raised surface at least partially covering the electrical connector 118. According to yet another embodiment, the protective housing 116 may advantageously protect a cable connector, which connects the optical probe 100 to external monitoring equipment. The foregoing cable connector is further disclosed with reference to FIGS. 5 and 6.

According to an embodiment of the invention, the protective housing 116 advantageously protects the electrical connector 118 from environment conditions external to the sensor. For example, according to one embodiment, the protective housing 116 may advantageously substantially seal the electrical connector 118 to the foregoing cable connector, thereby protecting the engaged connectors from fluids, dirt, ordinary wear and tear, or the like.

According to yet another embodiment, when the protective housing 116 is formed at least partially to fit the shape of a known external connector, such as the patient cable connector described with reference to FIGS. 5 and 6, the protective housing 116 may advantageously assist in creating a secure but removable electrical connection, through, for example, a substantially sealable or friction fit relationship.

Although disclosed with respect to preferred and alternative embodiments, a skilled artisan will recognize from the disclosure herein that the protective housing 116 may advantageously be mounted in a reverse direction as that shown in FIG. 1, in addition to be placed on the lower housing 104. Moreover, a skilled artisan will recognize from the disclosure herein that the protective housing 116 may be performed by the upper housing 102 or lower housing 104, when the foregoing housings are appropriately shaped to carry the electrical connector 118. Thus, it is foreseen that the functions of the protective housing 116 may advantageously be performed by any of the housings of the optical probe 100 in a wide number of configurations.

According to one embodiment, the protective housing 116 generally comprises the same or similar material formed and in the same or similar manner as that of the upper housing 102 or the lower housing 104.

FIG. 1 also shows the electrical connector 118. According to one embodiment, the electrical connector 188 comprises a flexible plastic tab 120 having a connection tab protrusion 122 with a locking aperture 124 and a flexible circuit 126. According to one embodiment, the flexible plastic tab 120 is rectangular in shape with the elongated portion of the rectangle being aligned with an elongated axis of the optical probe 100. According to one embodiment, one end of the tab 120 terminates in a semicircular tongue, thereby forming the connection tab protrusion 122. The connection tab protrusion 122 includes the locking aperture 124.

According to another embodiment, the tab 120 provides a durable yet flexible mounting surface for at least a portion of the flexible circuit 126. By using flexible materials, the tab 120 serves a shock absorbing function for movement, pushes and pulls on the optical probe 100, and connections made to the electrical connector 118. In addition, the connection tab protrusion 122 and a locking aperture 124 may advantageously serve as a tongue to substantially secure an electrical connection made between the electrical connector 118, and, for example, a patient cable connector. In addition, the locking aperture 124 provides a catch to prevent accidental unplugging of the electrical connector 118.

The foregoing tab 120 also advantageously guides a mating cable connector, such as those cables connectors connecting the optical probe 100 to external monitoring equipment, into secure, removable, electrical contact with the electrical connector 118. Through such connection, the tab 120 provides electrical communication between the external monitoring equipment and the light source or photodetector of the optical probe 100. Accordingly, the tab 120 advantageously provides a secure, plugable, connection between the electrical components of the sensor and external monitoring equipment. Furthermore, the tab 120 provides a shock absorbing connection between the optical probe 100 and an external connection. At the same time, the locking aperture 124 and the connection tab protrusion 122 provide a latch opening for a secure but removable locking mechanism securing the electrical connector 118 of the optical probe 100 to an external patient cable connector. According to one embodiment, the tab 120 comprises injection moldable thermoplastic material or other suitable medium.

Figure 2:
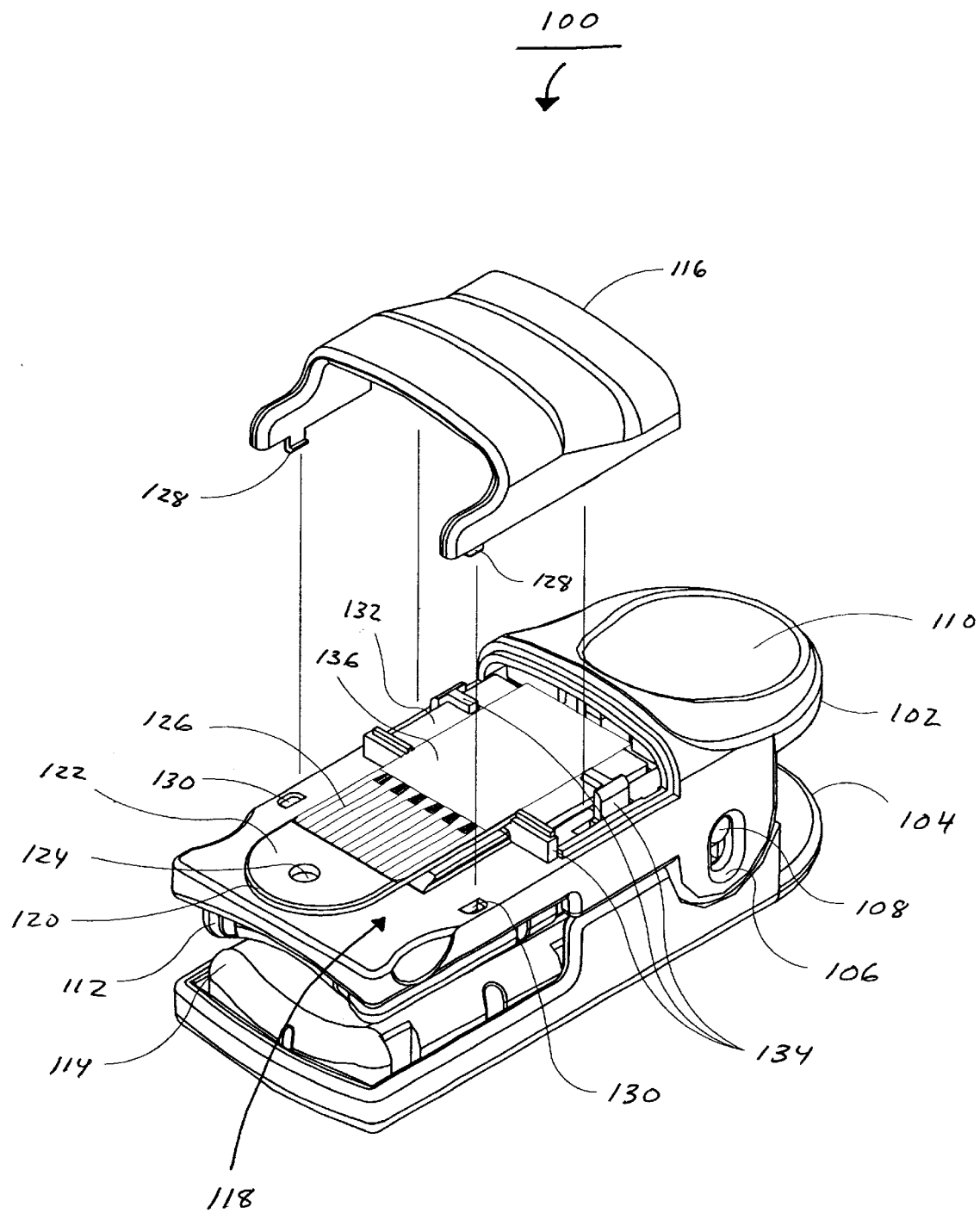
FIG. 2 is a perspective view of the optical probe of FIG. 1 with a protective housing raised above the probe housing, according to aspects of an embodiment of the present invention.

FIG. 2 illustrates the optical probe 100 with the protective housing 116 lifted from the upper housing 102. The protective housing 116 is in one embodiment attached to the upper housing 102 through a tab and aperture mechanism. For example, as shown in FIG. 2, the protective housing 116 may include securing tabs 128, such as detents or latches, which lock into apertures 130 on the upper housing 102. However, it is foreseen that the protective housing 116 may be attached by any commonly used means including plastic molding, locking components, screws, and the like. It is further foreseen that, in the absence of the protective housing 116, the flexible plastic tab 120 may advantageously directly connect to the upper housing 102.

FIG. 2 also shows one embodiment of the attachment of the electrical connector 118 to the optical probe 100. For example, in one embodiment of the electrical connector 118, the flexible plastic tab 120 comprises locking protrusions 132 protruding perpendicular to the general elongated shape of the tab 120. In addition, the upper housing 102 includes locking slots 134 designed to mate with the locking protrusions 132, thereby substantially securing the tab 120 to the upper housing 102. According to one embodiment, optical probe 100 includes multiple locking protrusions 132 and multiple corresponding locking slots 134, thereby decreasing potential lateral movement of the plastic tab 120 during electrical connection of electrical connector 118 to external monitoring equipment. A skilled artisan will recognize from the disclosure herein that the locking slots 134 may comprise a wide number of connection mechanisms, including, for example, plastic molding, locking components, screws, adhesive, staples, and the like.

According to yet another embodiment, the electrical connector 118, including the flexible plastic tab 120, may advantageously be at least partially raised or suspended between the upper housing 102 and the protective housing 116. Thus, the upper housing 102 and the protective housing 116 may advantageously together form a pocket or guide, within which the tab 120 protrudes to connect to appropriately shaped electrical mating devices. A skilled artisan will recognize that the electrical connector 118 may also be suspended within the upper housing 102 when the upper housing 102 is altered to perform the function of the protective housing 116.

Advantageously, the attachment of the electrical connector 118 to the upper housing 102 (or another housing) of the optical probe 100 allows the electrical connector to serve as a secure but removable electrical connection between the optical probe 100 and external monitoring devices, while at the same time allowing the electrical connector 118 to include a shock absorbing function against patient movement or other agitation of the optical probe 100.

Advantageously, the electrical connector 118 of FIG. 2 is connectable to cables provided, for example, for use with disposable optical probes. Thus, the electrical connector 118 allows users to choose the optical probe most suitable for a specific condition. For example, when a patient may have a particularly fluid or soiled condition, such as, for example, a burn victim, a health care provider may wish to use typically more expensive disposable optical probes. Once the patient has recovered to a less infecting or electronically damaging environment, the health care provider may advantageously change to the typically less expensive reusable probes, such as, for example, the optical probe 100 of the present invention, without changing the cables connected to the external monitoring equipment.

FIG. 2 also shows the electrical connector 118, and in particular, the flexible circuit 126 partially covered by one or more protective flaps 136. According to one embodiment of the invention, the flexible circuit 126 includes a number of conductive paths, each conductive path electrically connected to one or more electrical components, such as the light source or the detector. The conductive paths of the circuit may be made from any known conductor, such as silver, copper, and the like. As the conductive paths change from the pattern represented in the portion mating with an external monitoring equipment connector, to patterns designed to provide contacts with the various electrical components, the conductive paths, and therefore, the flexible circuit 126, are covered by the protective flaps 136. Accordingly, the protective flaps 136 advantageously guards against damage or electrical shorts in the conductive paths.

Figure 3A:
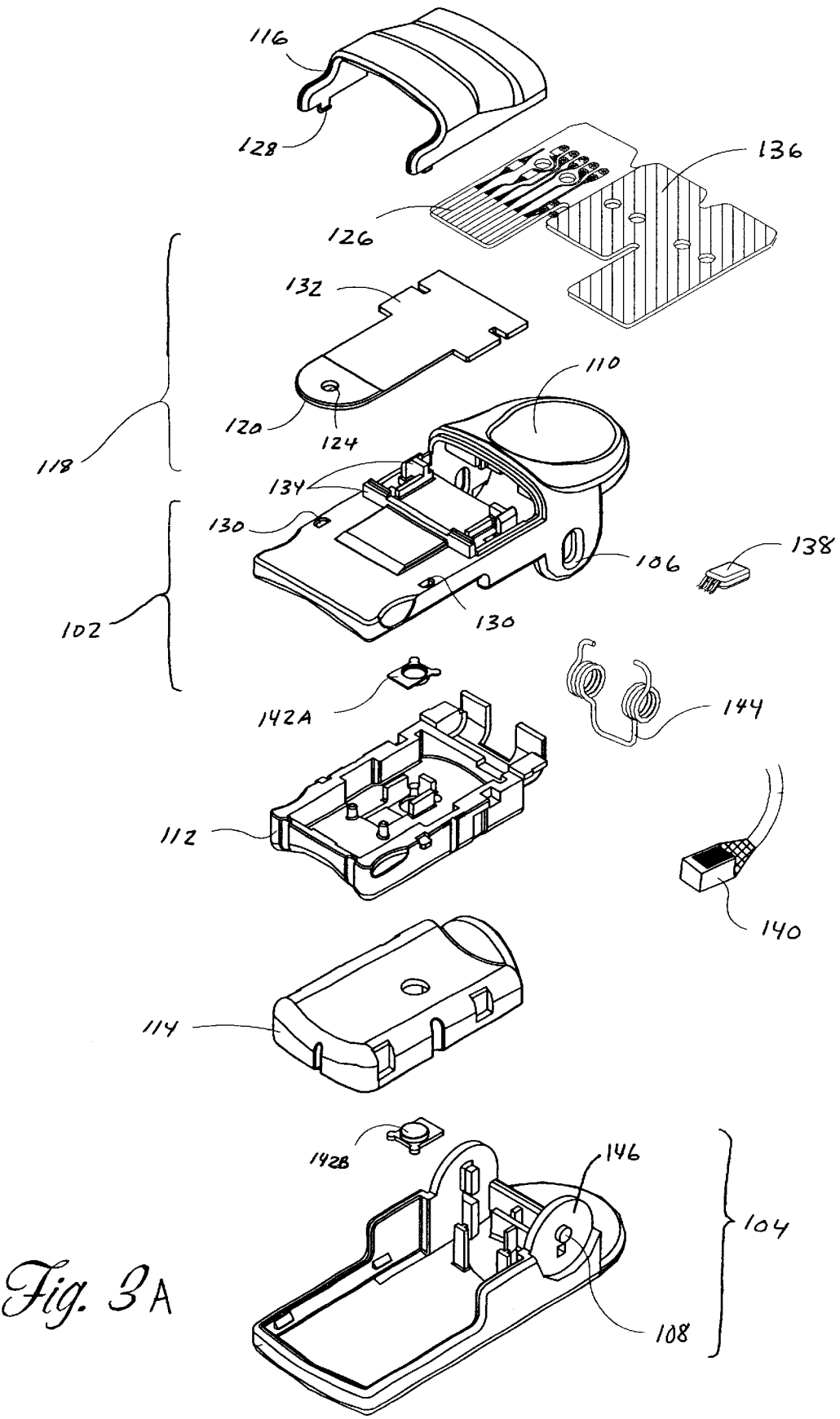
FIG. 3A is an exploded view of the optical probe of FIG. 1, according to aspects of an embodiment of the present invention.

FIG. 3A shows an exploded view of the optical probe 100 of the present invention including the electrical connector 118. For example, FIG. 3A emphasizes an embodiment of the protective flaps 136 and how, according to that embodiment, the protective flaps 136 may be folded to create a faraday shield for the flexible circuit 126, thus protecting it from electromagnetic interference.

Advantageously, the optical probe 100 with the electrical connector 118 thus provides electrical power and signals to and from the optical probe 100 to external monitoring devices via the electrical connector 118 in a secure, interchangeable, replaceable, shock absorbing, and universal manner. For example, the optical probe 100, an external cable connector or another compatible connector, and in one embodiment the electrical connector 118, may advantageously be independently replaceable, such that failure or ware of one component does not require replacement of other related components.

FIG. 3A also shows the optical probe 100, and in particular, the upper housing 102, comprising one or more light emitting diodes (LEDs) 138, although it will be appreciated that other light generating devices may be used. The LEDs 138 provide a light source for the optical probe 100 and are electrically connected to the flexible circuit 126 through the conductive path and one or more wires. The construction and operation of the LEDs and their drive circuitry is described in U.S. Pat. No. 5,758,644 incorporated herein by reference.

FIG. 3A also shows the optical probe 100, and in particular, the lower housing 104, comprising a detector 140, such as a photodetector, designed to detect an amount of light energy passed from the LEDs 138, through the tissue at the measurement site. For example, the LEDs 138 may shine light energy through an aperture in the upper housing 102, through the patient tissue, then through an aperture in the lower housing 104 and onto the detector 140. Alternatively, a skilled artisan will recognize from the disclosure herein that the optical probe 100 may incorporate housing adapted for a reflective detector. However, the detector 140 shown in FIG. 2, is attached to internal winng eventually electrically communicating with one or more of the conductive paths on the flexible circuit 126.

FIG. 3A also illustrates the optical probe 100 having multiple transparent covers 142A and 142B, preferably comprising transparent polymer, which act as protection for the LEDs 138 and the detector 140. The construction and operation of the covers 142, including the potential of including physical and optical properties or characteristics therein, is described in U.S. patent application Ser. No. 09/420,544, incorporated by reference herein in the foregoing disclosure.

According to yet another embodiment, the optical probe 100 includes a biasing spring 144 preloaded or partially wound so as to bias the upper housing 102 against the lower housing 104, thereby biasing the open end of the optical probe 100 into a closed position around the tissue at the measurement site, for example, around the digit of a patient. In this manner, the finger recesses 110 allow a user to grasp the optical probe 100 between their fingers and apply force counter to the biasing spring 144, thereby opening the open end of the optical probe 100 for insertion of, for example, the distal end of a digit.

According to yet another embodiment, the lower housing 104 also comprises opposing vertical risers 146, each including at least one of the pivoting elements 108. As mentioned in the foregoing, when the lower housing 104 and the upper housing 102 are coupled, the pivoting element 108 and the aperture 106 form a pivoting hinge-like joint which allows the optical sensor to comfortably adjust position while maintaining the proper geometry between the patient tissue, in this case a digit, the light source and the photodetector.

Based on the foregoing, the optical probe 100 with the electrical connector 118 provides electrical power and signals to and from the optical probe 100 to external monitoring devices via the electrical connector 118 in a secure, interchangeable, replaceable, shock absorbing, and universal manner. Moreover, according to some embodiments, the electrical connector 118 and the optical probe 100 are independently replaceable, so failure or ware of one component does not require replacement of other related components.

FIG. 3B shows an exploded view of another embodiment of the optical probe 100 of the present invention including the electrical connector 118. As shown in FIG. 3B, the optical probe 100 is similar to that of FIG. 3A. However, in one embodiment of the optical probe 100, the flexible circuit 126 includes flexible circuit extensions 204 and 206. The flexible circuit extension 204 extends the flexible circuit 126 to the LED 138. Similarly, the other flexible circuit extension 206 extends the flexible circuit 126 to the photodetector 140. The flexible circuit extensions 204 and 206 are part of the flexible circuit 126, and are constructed from the same or similar materials.

Advantageously, the flexible circuit extensions 204 and 206 reduce the construction cost of the optical probe 100 by removing the need for any number of wires to be added and connected to any number of sensor elements. In addition, the substantially flat flexible circuit extensions 204 and 206 do not hinder the flexibility of the optical sensor at the hinge-like joint.

Furthermore, the flexible circuit 126 in one embodiment includes a coding resistor 202 in parallel with the LED 138. The resistor 262 is used, for example, to indicate the type of optical probe 100. In other words, the value of the coding resistor 202 can be selected to indicate that the optical probe 100 is an adult probe, a pediatric probe, a neonatal probe, a disposable probe, a reusable probe, or the like. The coding resistor 202 is also utilized for security purposes. In other words, the value of the coding resistor 202 is used to indicate that the optical probe 100 is from an authorized sensor supplier. This permits control over safety, quality, and performance concerns which arise with unauthorized sensors. In addition, the coding resistor 202 is used to indicate physical or operating characteristics of the optical probe 100, such as the wavelengths of the LED 138. Additional disclosure related to uses and specific embodiments of the resistor 202 can be found in U.S. patent application Ser. No. 09/404,060, filed Sep. 23, 1999, entitled "PULE OXIMETRY SENSOR ADAPTER," commonly assigned to the assignee of the present application and incorporated herein by reference. The coding resistor 202 provided can be read by an external monitoring system, such as that described in pending U.S. patent application Ser. No. 08/478,493, filed Jun. 7, 1995, entitled "MANUAL AND AUTOMATIC PROBE CALIBRATION," now U.S. Pat. No. 5,758,644 and assigned to the assignee of the present application.

Figure 4:
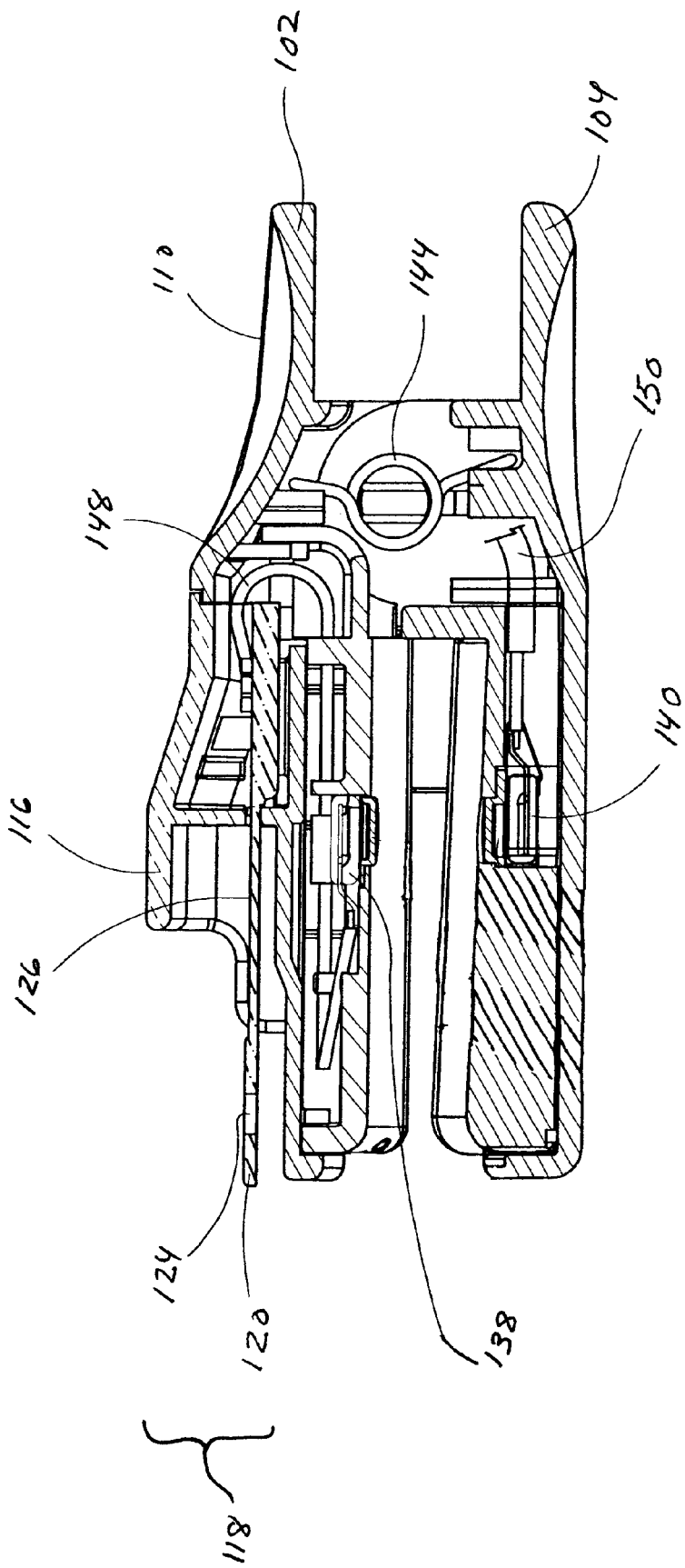
FIG. 4 is a cross-sectional view of the optical probe of FIG. 1, according to aspects of an embodiment of the present invention.

FIG. 4 shows a cross sectional view of one embodiment of the optical probe 100 of the present invention with the electrical connector 118. As shown in FIG. 4, the flexible plastic tab 120 is housed between the protective housing 116 and the upper housing 102. According to this embodiment, the flexible plastic tab 120, including the connection tab protrusion 122, the locking aperture 124, are advantageously accessible to the environment outside of the optical probe 100.

Further, FIG. 4 shows one or more of the conductive paths on the flexible circuit 126 are connected by a first internal wire 148 to the LEDs 138 housed within the upper housing 102. In addition, FIG. 4 shows one or more of the conductive paths on the flexible circuit 126 being connected by a second internal wire 150 to the detector 140 housed within the lower housing 104. Moreover, the cross sectional view of FIG. 4 illustrates the biasing spring 144 being positioned and biased between the upper housing 102 and the lower housing 104 to provide resistance and tension as disclosed in the foregoing.

FIG. 4 also illustrates the protective housing 116, in one embodiment, partially protecting the electrical connector 118 as the electrical connector 118 is at least partially suspended between the protective housing 116 and upper housing 102, thereby providing ease of connectability along with 360° degrees of support for the connection. For example, the connection is supported beneath by the cable connector being in contact with the upper housing 102, from the sides and above by contact with the protective housing 116, and from the center by the electrical contact 118. In addition to the foregoing, skilled artisans can foresee from the disclosure herein, alternative embodiments such as alternative placements of the electrical connector 118 in alternative directions or use of the lower housing 104.

Figure 5:
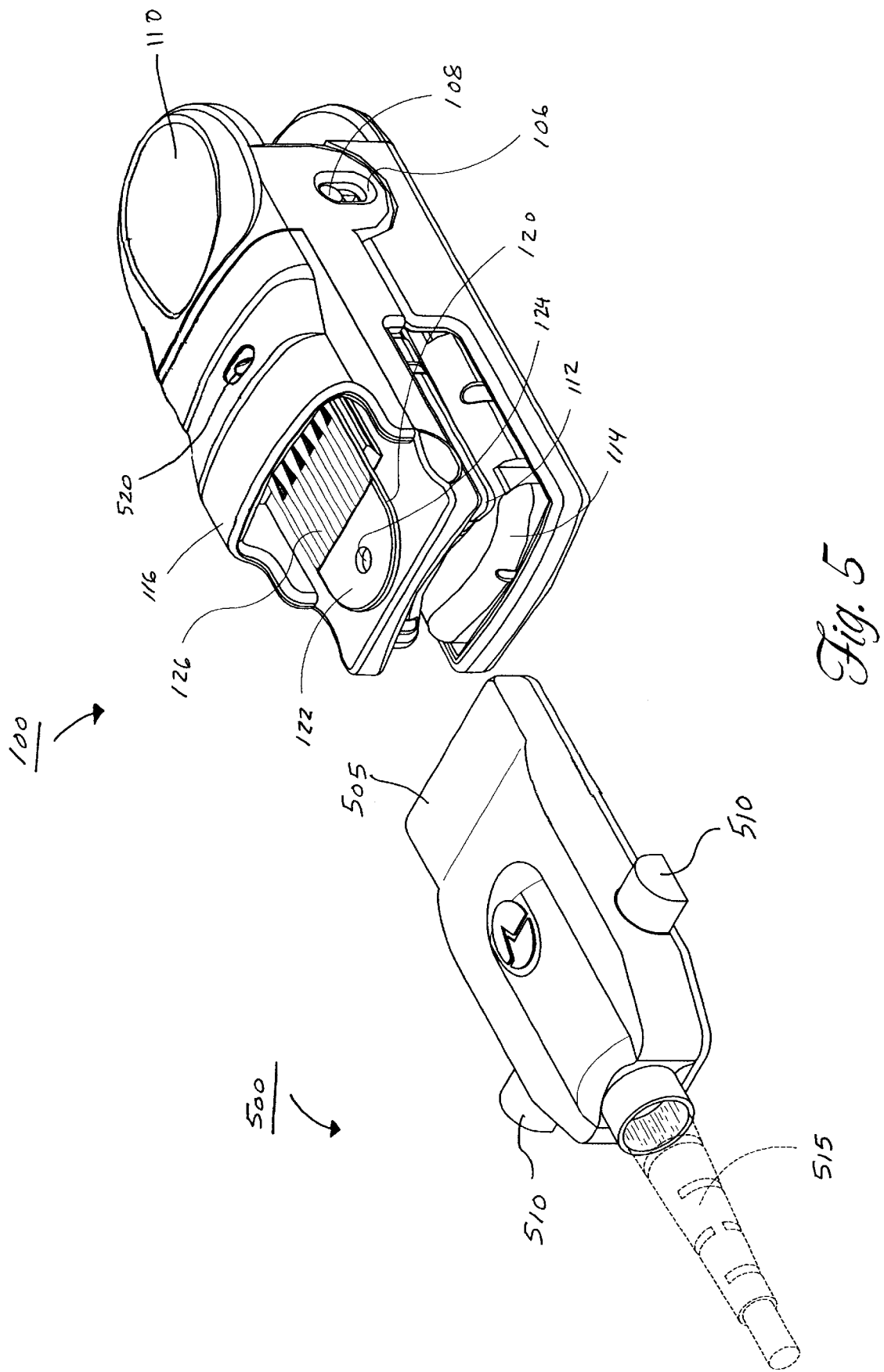
FIG. 5 is a perspective view of the optical probe of FIG. 1 with a patient cable connector, according to aspects of an embodiment of the present invention.

FIG. 5 shows the optical probe 100 of the present invention including the electrical connector 118 in one embodiment where an external plug, such as, for example, a patient cable connector 500 is adapted to securely and releasably form a plugable electrical connection. For example, FIG. 5 shows the patient cable connector 500 having a receptor end 505, a releasing mechanism 510, and external wire 515. According to one embodiment, the receptor end 505 is designed to electrically mate with the electrical connector 118 of the instant invention. For example, the receptor end 505 may advantageously include electrical contacts that, when the patient cable connector 500 engages the optical probe 100, the electrical contacts line up and electrically communicate with conductive paths on the flexible circuit 126. The electrical contacts in the patient cable connector 500 then communicate with the external wire 515 to communicate signals to and from external monitoring equipment (not shown). The construction and operation of the patient cable connector, its electrical contacts and circuitry, as well as the release mechanism 510, is described in U.S. Pat. No. 5,934,925, incorporated by reference in the foregoing.

According to one embodiment, the shape of the connection tab protrusion 122 is adjusted to fit snugly with the patient cable connector 500, and the internal shape (in this case, concave) of the protective housing 116 is adapted to snugly fit the external surface of the patient cable connector 500. According to one embodiment, the protective housing 116, the tab 122, and the contacts of the patient cable connector 500 work together to form a friction fit relationship firmly securing the connector 500 to the optical probe 100.

According to one embodiment, once the patient cable connector 500 has been connected to the electrical connector 118, the flexible plastic tab 120 is locked into place within the connector 500 via the locking aperture 124 on the tab 120. The resulting connection is advantageously flexible, but electrically secure. For example, the foregoing connection prohibits accidental pulls or patient agitation from dislodging the electrical connection while maintaining relatively easy release of the connection through the locking mechanism. Thus, the foregoing connection provides a flexible but secure connection, thereby ensuring jolts, accidental pulls, or patient agitation have a reduced impact on the secure operation of the optical probe 100.

FIG. 5 also shows a sensor life indicator 520, according to additional embodiments of the invention. For example, the indicator 520 may advantageously comprise one or more LED's designed to indicate to the user that the useful life of the optical probe 100 has expired, due to ware, overuse, malfunction, or the like. According to one embodiment, the determination of the useful life is made within circuitry of the optical probe 100. For example, the optical probe 100 may advantageously include one or more memory registers or counters for storing an indication of the use of the optical probe 100. For example, the memory registers may count the number of drive pulses received by the optical probe 100, the number of return signals generated by the detector 140, use any number of known oscillators or oscillating circuits to generate a measure of time or use, or the like. According to this embodiment, once the data stored in the memory registers reaches a predetermined threshold, the sensor life indicator 520 is activated, such as, for example, the emission of a constant or blinking light, such as, for example, a red light.

According to one embodiment, the determination of the useful life of the optical probe 100 may advantageously be made using the external monitoring equipment, or a combination of the optical probe 100 and the external monitoring equipment. In such embodiments, a signal may advantageously be passed from the external monitoring equipment to the sensor life indicator 520 for activation thereof. Additional disclosure and specific embodiments of the sensor life indicator 520 may advantageously be found in U.S. patent application Ser. No. 09/502,032 filed Feb. 10, 2000, entitled "SENSOR LIFE MONITOR SYSTEM," commonly assigned to the assignee of the present application and incorporated herein by reference.

A skilled artisan will recognize from the disclosure herein that the sensor life indicator 520 can be implemented in a number of alternative embodiments. For example, the sensor life indicator 520 can be visible through an aperture on the patient cable connector 500, can be integrated with the flexible circuit 126, and may advantageously be place virtually on any housing or extension of the optical probe 100. Moreover, the sensor life indicator 520 may advantageously provide an indication of proper use, continued usefulness, proper application, or the like, through the use of another signal, such as, for example, a green light.

As discussed in the forgoing, the sensor life indicator 520 advantageously permits a user of the optical probe 100 to recognize when the useful life of the probe's components is near an end due to ware, overuse, or the like. Without the sensor life indicator 520, the user can only approximate or guess when the optical probe 100 should be replaced, or wait until the optical probe 100 ceases to function properly.

Figure 6:
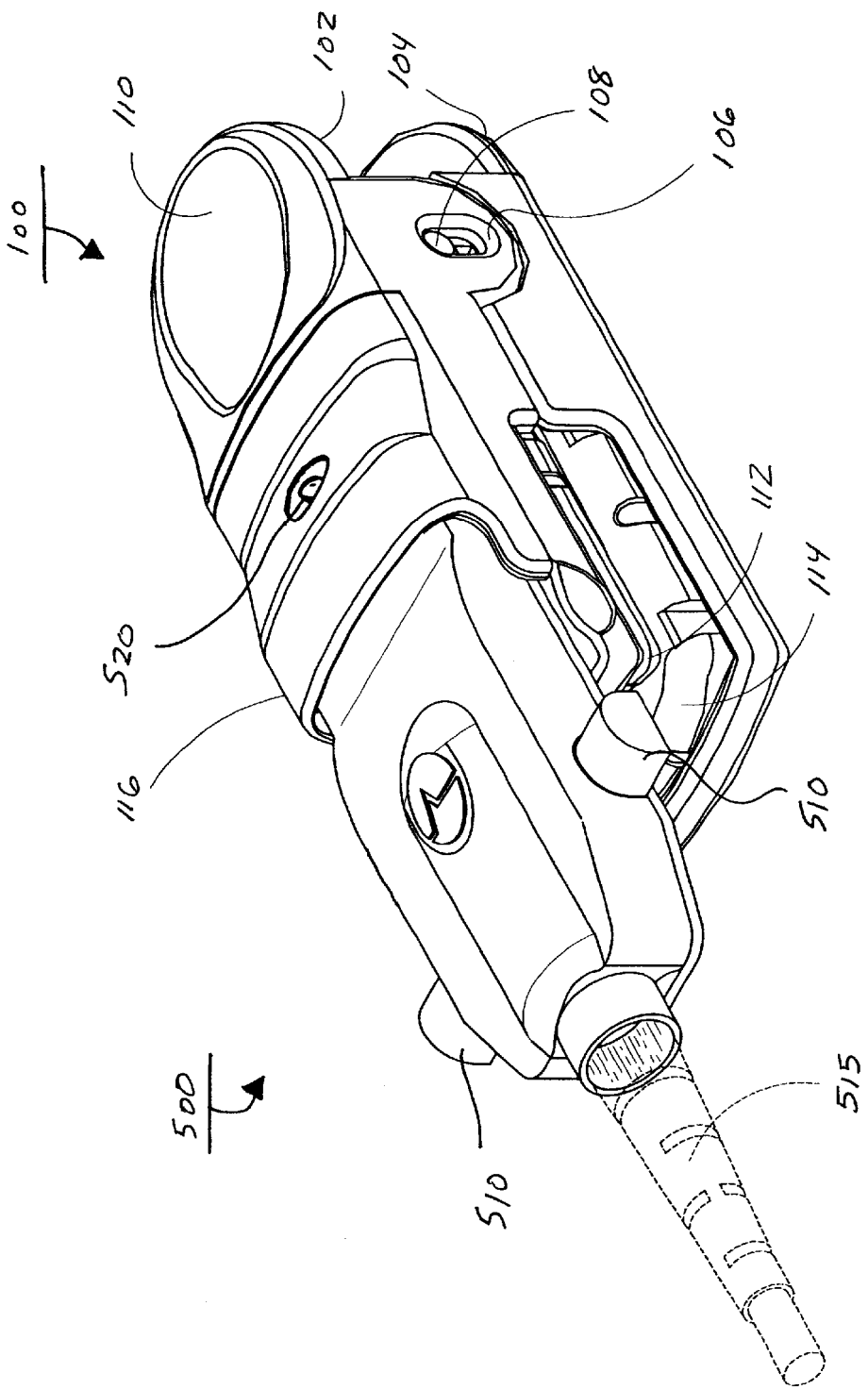
FIG. 6 is a perspective view of the optical probe of FIG. 1 engaged to the patient cable connector of FIG. 5, according to aspects of an embodiment of the present invention.

FIG. 6 shows the patient cable connector 500 engaged with or attached to the optical probe 100, according to one embodiment of the invention. The optical probe 100, in one embodiment, includes the sensor life indicator 520. According to one embodiment, the patient cable connector 500 may advantageously be locked in an engaged position through the locking aperture 124. According to yet another embodiment of the invention, the patient cable connector 500 and the optical probe 100 form a substantially secure, yet releasable, seal. According to one embodiment, the seal may be resistant to fluids or the like.

The probe of the present invention may be employed in any circumstance where a measurement of transmitted or reflected energies is to be made, including but not limited to, measurements taken on a finger, an earlobe, a lip or a forehead and the like. Similarly, a skilled artisan will recognize from the disclosure herein that the electrical connection 118 may be adjusted to any number of embodiments foreseen by the present invention. For example, a skilled artisan will recognize from the disclosure herein that the electrical connector 118 may be attached to the lower housing 104, may be secured in an opposite or rotatable manner via a wide number of securement mechanisms, including those disclosed herein, hook-and-loop material, releasable or other latches, rotating securement mechanisms, or the like. Moreover, a skilled artisan will recognize from the disclosure herein the option of reversing components, for example, placing various components of the electrical connector 118 on the patient cable connector 500 and vice versa. In addition, the locking mechanism may include any number of a wide variety of known devices, such as, for example, thumb screws, hook-and-latch materials, straps, press or friction fit mechanisms, or the like.

In addition, a skilled artisan will recognized a wide number of other embodiments from the disclosure herein, including but not limited to, changes in the shape of the optical probe 100 and its components, changes in shape to the flexible circuit 126, or the like. In addition, different placement of the flexible circuit 126 upon the device and different shapes or positions of the protective housing 116, when the protective housing 116 is used at all, are foreseen. Moreover, the described embodiments are to be considered in all respects, only as illustrative and not restrictive. The scope of the invention therefore is indicated by the appended claims rather than by the foregoing description.

What is claimed is:

1. An optical probe for irradiating tissue and producing a signal indicative of a physiological parameter of the tissue, the optical probe comprising:

a housing substantially securing a light source and a detector to tissue at a measurement site, thereby allowing the detector to produce a signal indicative of at least one physiological parameter of the tissue; and a plugable electrical connector forming a releasable connection with a cable connector, wherein the electrical connector includes a plurality of conductive paths electrically communicating with the light source and the detector, and the cable connector electrically communicates with external monitoring equipment.

2. The optical probe of claim 1, wherein the electrical connector further comprises a durable tab designed to guide the cable connector into electric communication with the light source and detector.

3. The optical probe of claim 2, wherein at least a portion of the conductive paths mount to the durable tab.

4. The optical probe of claim 2, wherein the electrical connector further comprises a flexible circuit having the plurality of conductive paths.

5. The optical probe of claim 2, wherein the durable tab further comprises a locking mechanism.

6. The optical probe of claim 1, wherein the electrical connector further comprises a locking mechanism.

7. The optical probe of claim 1, wherein the optical probe further comprises a protective housing at least partially covering the electrical connector.

8. The optical probe of claim 1, wherein when the cable connector is engaged to the electrical connector of the optical probe, a protective housing at least partially covers the cable connector.

9. The optical probe of claim 1, the optical probe further comprising a sensor life indicator.

10. The optical probe of claim 1, the optical probe further comprising a coding resistor.

11. A reusable pulse oximetry sensor for producing a signal indicative of at least one physiological parameter of tissue, the sensor comprising:
    an upper housing having
        a first circuit element comprising one of a light source and a detector, and
        a first wire connected to the first circuit element;
    a lower housing having
        a second circuit element comprising the other of the light source and the detector, and
        a second wire connected the second circuit element;
    a hinge-like joint adjustably coupling the upper housing and lower housing; and
    an electrical connector having
        a tab, and
        a flexible circuit mounted on the tab and comprising a plurality of conductive paths,
    wherein one of the conductive paths electrically connects to the first wire while another of the conductive paths electrically connects to the second wire, thereby providing a electrical connection from the conductive paths of the electrical connector to the light source and the detector.

12. The sensor of claim 11, further comprising a protective housing.

13. The sensor of claim 12, wherein the protective housing at least partially covers the electrical connector.

14. The sensor of claim 12, wherein the electrical connector is adapted to form a plugable electrical connection with a cable connector electrically communicating through a cable to external monitoring equipment, and wherein the protective housing is adapted to substantially seal the electrical connection against external environment conditions when the cable connector is coupled to the electrical connector.

15. The sensor of claim 11, wherein the electrical connector is adapted to form a plugable electrical connection with a cable connector electrically communicating through a cable to external monitoring equipment, and wherein the electrical connector includes a locking mechanism releasably engaging the electrical connection to the cable connector.

16. The sensor of claim 15, wherein the locking mechanism comprises locking aperture on the tab.

17. The sensor of claim 11, wherein the upper housing includes an upper support surface substantially aligning the first circuit element to a measurement site.

18. The sensor of claim 17, wherein the measurement site comprises a portion of a human digit.

19. The sensor of claim 11, wherein the lower housing includes a lower support surface substantially aligning the second circuit element to a measurement site.

20. The sensor of claim 19, wherein the measurement site comprises a portion of a human digit.

21. The sensor of claim 11, wherein at least one of the upper housing and lower housing includes a finger recess for operating the hinge-like joint.

22. A reusable pulse oximetry sensor for producing a signal indicative of at least one physiological parameter of tissue, the sensor comprising:
    an upper housing having a first circuit element comprising one of a light source and a detector;
    a lower housing having a second circuit element comprising the other of the light source and the detector;
    a hinge-like joint adjustably coupling the upper housing and lower housing; and
    an electrical connector having
        a tab, and
        a flexible circuit mounted on the tab and comprising a plurality of conductive paths,
    wherein one of the conductive paths electrically connects to the detector while another of the conductive paths electrically connects to the light source.

23. The sensor of claim 22, further comprising a protective housing.

24. The sensor of claim 23, wherein the protective housing at least partially covers the electrical connector.

25. The sensor of claim 23, wherein the electrical connector is adapted to form a plugable electrical connection with a cable connector electrically communicating through a cable to external monitoring equipment, and wherein the protective housing is adapted to substantially seal the electrical connection against external environment conditions when the cable connector is coupled to the electrical connector.

26. The sensor of claim 22, wherein the electrical connector is adapted to form a plugable electrical connection with a cable connector electrically communicating through a cable to external monitoring equipment, and wherein the electrical connector includes a locking mechanism releasably engaging the electrical connection to the cable connector.

27. The sensor of claim 26, wherein the locking mechanism comprises locking aperture on the tab.

28. The sensor of claim 22, wherein the upper housing includes an upper support surface substantially aligning the first circuit element to a measurement site.

29. The sensor of claim 28, wherein the measurement site comprises a portion of a human digit.

30. The sensor of claim 22, wherein the lower housing includes a lower support surface substantially aligning the second circuit element to a measurement site.

31. The sensor of claim 30, wherein the measurement site comprises a portion of a human digit.

32. The sensor of claim 22, wherein at least one of the upper housing and lower housing includes a finger recess for operating the hinge-like joint.

33. The sensor of claim 22, wherein the flexible circuit includes layers of silver circuitry.

34. The sensor of claim 22, the sensor further comprising a coding resistor.

35. The sensor of claim 22, the sensor further comprising a sensor life indicator.

36. An optical probe for non-invasively collecting a signal indicative of a physiological parameter of tissue, the optical probe comprising:

a light source;

a detector;

a connector having a flexible circuit mounted on a durable tab; and a protective housing at least partially covering the flexible circuit mounted on the durable tab.

37. The optical probe of claim 36, further comprising including a locking mechanism adapted to releasably secure the connector to a cable connected to external monitoring equipment.

38. A method of determining a physiological parameter of tissue using a non-invasive optical probe, the method comprising:

positioning a light source of a non-invasive optical probe to irradiate a measurement site with light;

positioning a detector of the probe to detect light which interacts with the measurement site; and releasably connecting an external monitoring equipment cable to the probe through a flexible circuit mounted on a durable tab having a protective cover;

wherein at least one the conductive paths electrically communicates with the light source and at least one of the conductive paths electrically communicates with the detector.

39. The method of claim 38, wherein the releasably connecting includes locking the probe to the cable through a locking mechanism.

40. The method of claim 38, further comprising verifying that an indicia signal does not indicate that the optical probe should not be used.

41. The method of claim 40, wherein the verification is performed by a sensor life indicator.

42. The method of claim 38, further comprising signaling a unique code to external monitoring equipment.

43. The method of claim 42, wherein the signaling is performed by a coding resistor.

\* \* \* \* \*